United States Patent [19]
Gaglani et al.

[11] Patent Number: 6,140,370
[45] Date of Patent: Oct. 31, 2000

[54] STABILIZED ALKYD BASED COMPOSITIONS CONTAINING HALOPROPYNL COMPOUNDS

[75] Inventors: Kamlesh D. Gaglani, Belle Mead; Meihua Yang, Hillsborough Township, both of N.J.

[73] Assignee: Troy Technology Corporation, Inc., Wilmington, Del.

[21] Appl. No.: 09/157,861

[22] Filed: Sep. 21, 1998

[51] Int. Cl.⁷ .......................... A01N 37/18; A61K 31/165
[52] U.S. Cl. .......................... 514/617; 514/625; 514/627; 564/305
[58] Field of Search .............................. 564/305; 514/617, 514/625, 627

[56] References Cited

U.S. PATENT DOCUMENTS

| | | | |
|---|---|---|---|
| 3,660,499 | 5/1972 | Kobayashi et al. | 260/613 D |
| 3,923,870 | 12/1975 | Singer | 260/482 C |
| 4,018,661 | 4/1977 | Cramer et al. | 106/15 |
| 4,259,350 | 3/1981 | Morisawa et al. | 424/308 |
| 4,276,211 | 6/1981 | Singer et al. | 260/29.6 |
| 4,297,258 | 10/1981 | Long, Jr. | 260/27.6 |
| 4,323,602 | 4/1982 | Parker | 427/298 |
| 4,592,773 | 6/1986 | Tanaka et al. | 71/88 |
| 4,616,004 | 10/1986 | Edwards | 514/63 |
| 4,639,460 | 1/1987 | Rose | 514/369 |
| 4,719,227 | 1/1988 | Shade et al. | 514/452 |
| 4,915,909 | 4/1990 | Song | 422/28 |
| 4,945,109 | 7/1990 | Rayudu | 514/478 |
| 4,977,186 | 12/1990 | Gruening | 514/479 |
| 5,071,479 | 12/1991 | Gruening | 106/18.32 |
| 5,082,722 | 1/1992 | Gugliemo, Sr. | 428/255 |
| 5,127,934 | 7/1992 | Mattox | 71/67 |
| 5,190,580 | 3/1993 | Gruening | 106/18.32 |
| 5,209,930 | 5/1993 | Bowers-Daines et al. | 424/401 |
| 5,554,784 | 9/1996 | Gruening | 560/107 |

FOREIGN PATENT DOCUMENTS

| | | |
|---|---|---|
| 2138292 | 10/1984 | United Kingdom . |
| 2140299 | 11/1984 | United Kingdom . |

*Primary Examiner*—Dwayne C. Jones
*Attorney, Agent, or Firm*—Robert F. Tavares

[57] ABSTRACT

This invention pertains to the protection of nonaqueous compositions containing a transition metal from microbial spoilage using a stabilized antimicrobial composition comprising a halopropynyl compound and an organic epoxide.

35 Claims, No Drawings

STABILIZED ALKYD BASED COMPOSITIONS CONTAINING HALOPROPYNL COMPOUNDS

BACKGROUND OF THE INVENTION

1. Field of the Invention

The present invention pertains to antimicrobial compositions that are stable in the presence of transition metals, nonaqueous compositions containing a transition metal and the antimicrobial composition, and a method for protecting a substrate from microbial infestation with the antimicrobial composition. The antimicrobial composition comprises a halopropynyl compound and an organic epoxide.

2. Description of the Background

Both exterior and interior surfaces, substrates of all types and organic compositions and formulations, when exposed to common environmental conditions, are prone to attack, discoloration and various kinds of destruction by a variety of species of microorganisms, including fungi, algae, bacteria and protozoa. As a result, there has always been a great need for effective and economical means to protect commercial compositions and formulations from the deterioration and destruction caused by such microorganisms, and to do so for an extended period of time.

There are a variety of materials which need protection against such microorganisms including, for example, materials such as paints and other coating formulations, surfactants, proteins, starch-based compositions, inks, emulsions and resins, stucco, concrete, stone, and cementaceous surfaces, wood, caulking, sealants, leather, plastics, and textiles. Other important commercial materials such as polymer dispersions or aqueous latex paints containing polyvinyl alcohol, polyacrylates or vinylpolymers, thickener solutions containing cellulose derivatives, kaolin suspensions and metal working fluids, also are prone to degradation by the action of objectionable microorganisms, which can significantly impair the usefulness of such compositions. Such degradation may produce, inter alia, changes in pH values, gas formation, discoloration, the formation of objectionable odors, and/or changes in rheological properties.

Wooden objects, in particular, are subject to degradation from a wide variety of natural pests. Fungi are particularly prevalent and include brown rots, white rots and soft rots. Fortunately, a variety of compositions have been developed for treating wooden objects and other materials and surfaces to retard the destructive effect of such pests.

A great deal of effort has gone into developing a wide variety of materials which, to various degrees, are effective in retarding or preventing the growth of, and accompanying destruction caused by, such microbes in a variety of circumstances. Such antimicrobial compounds include halogenated compounds, organometallic compounds, quaternary ammonium compounds, phenolics, metallic salts, heterocyclic amines, formaldehyde donors, organosulfur compounds and the like.

One of the most effective and best known classes of biocides used in such compositions are those containing a halopropynyl moiety, and especially an iodopropynyl moiety. Such compounds are widely disclosed in the patent literature including U.S. Pat. Nos. 3,660,499; 3,923,870; 4,259,350; 4,592,773; 4,616,004 and 4,639,460 to name a few. Included within this class of compounds are the halopropynyl carbamates which are known primarily for their fungicidal activity. Among these is 3-iodo-2-propynyl butyl carbamate, also referred to as IPBC, which is one of the best known and probably the most widely used of the halopropynyl carbamate fungicides. It is a highly active broad spectrum fungicide and, in addition to its fungicidal activity, it has also been associated with algaecidal activity as disclosed in Great Britain Patent 2,138,292 and U.S. Pat. Nos. 4,915,909 and 5,082,722.

Despite their wide acceptance, the halopropynyl carbamate biocides have been reported to be prone to degradation under certain conditions. In many of these instances, the degradation is minor, and while it may sometimes result in some discoloration and yellowing, a sufficient degree of antimicrobial protection usually remains.

A different and more significant form of degradation appears to occur in the presence of transition metals. Certain transition metals appear to cause significant destruction of halopropynyl compounds which can result in the loss of their ability to prevent microbial growth. This can be particularly troublesome in alkyd based coating systems where transition metals are used routinely in a number of pigments and, more importantly, in drier systems. The use of transition metals in such solvent based systems can cause a slow, but definite, degradation of the halopropynyl compounds. For this reason, the use of halopropynyl compounds as antimicrobial agents in nonaqueous compositions containing transition metals, especially alkyd coating compositions, has been disfavored.

The present invention addresses the destruction of halopropynyl compounds in the presence of certain transition metals and provides means for inhibiting said destruction.

BRIEF DESCRIPTION OF THE INVENTION

The present invention is directed to antimicrobial compositions comprising a halopropynyl compound and an organic epoxide, such compositions being stable in the presence of transition metals.

In another embodiment, the present invention is directed to a nonaqueous composition containing a transition metal and an antimicrobial composition comprising a halopropynyl compound and an organic epoxide.

In yet another embodiment, the present invention is directed to an alkyd coating composition, especially an alkyd paint, containing a transition metal and an antimicrobial composition comprising a halopropynyl compound and an organic epoxide.

In yet another embodiment, the present invention is directed to a method for inhibiting microbial infestation in an alkyd coating composition containing transition metals which comprises incorporating therein an antimicrobial composition comprising a halopropynyl compound and an organic epoxide.

DETAILED DESCRIPTION OF THE INVENTION

The present invention is directed to the stabilization of antimicrobial halopropynyl compounds in nonaqueous systems containing transition metals.

Halopropynyl compounds that can be stabilized in accordance with the present invention are well known and can be generally identified by the following structure:

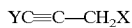

wherein Y is a halogen, preferably iodine, and X can be (1) oxygen which is part of an organic functional group; (2) nitrogen which is part of an organic functional group; (3)

sulfur which is part of an organic functional group; or (4) carbon which is part of an organic functional group.

The functional group of which oxygen is a part, is preferably an ether, an ester, or a carbamate group. The functional group of which nitrogen is a part is preferably an amine, an amide, or a carbamate group. The functional group of which sulfur is a part is preferably a thiol, a thiane, a sulfone, or a sulfoxide group. The organic functional group of which carbon is a part is preferably an ester, a carbamate or an alkyl group.

Examples of compounds which may be used as the halopropynyl compound of this invention are especially the active iodopropynyl derivatives. In this regard, please see U.S. Pat. Nos. 3,923,870; 4,259,350; 4,592,773; 4,616,004; 4,719,227; and 4,945,109, the disclosures of which are herein incorporated by reference. These iodopropynyl derivatives include compounds derived from propynyl or iodopropynyl alcohols such as the esters, acetals, carbamates and carbonates and the iodopropynyl derivatives of pyrimidines, thiazolinones, tetrazoles, triazinones, sulfamides, benzothiazoles, ammonium salts, carboxamides, and ureas. Preferred among these compounds is the halopropynyl carbamate, 3-iodo-2-propynyl butyl carbamate. This compound is included within the useful class of compounds having the generic formula.

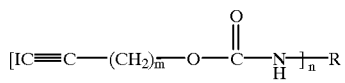

wherein R may have one to three linkages corresponding to n and is selected from the group consisting of hydrogen, substituted and unsubstituted alkyl groups having from 1 to 20 carbon atoms, substituted and unsubstituted aryl, alkylaryl, and aralkyl of from 6 to 20 carbon atoms or cycloalkyl and cycloalkenyl groups of from 3 to 10 carbon atoms, and m and n are independently integers from 1 to 3, i.e., they are not necessarily the same.

Particularly preferred are formulations of such halopropynyl carbamates where m is 1 and n is 1 and which have the following formula:

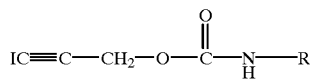

Suitable R substituents include alkyls such as methyl, ethyl, propyl, n-butyl, t-butyl, pentyl, hexyl, heptyl, octyl, nonyl, decyl, dodecyl, and octadecyl; cycloalkyls such as cyclohexyl; aryls, alkaryls and aralkyls such as phenyl, benzyl, tolyl, and cumyl; halogenated alkyls and aryls, such as chlorobutyl and chlorophenyl; and alkoxy aryls such as ethoxyphenyl and the like.

Especially preferred are such iodopropynyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

It has been found that halopropynyl compounds are subject to degradation in the presence of certain transition metals. While it is believed that most transition metals may have some detrimental effect on halopropynyl compounds, it has been found that some of the more commonly used metals are particularly troublesome. As a result the use of iodopropynyl compounds such as 3-iodo-2-propynyl butyl carbamate has been disfavored in substrates and compositions wherein the presence of certain transition metals, e.g. manganese, cerium, copper, iron, vanadium, chromium, cobalt, nickel and zinc, may affect its stability. This is particularly important in coating compositions such as oil based paints, wherein such transition metals are used as driers (e.g. Ce, Co, Mn, V) or are used as part of a pigment system (e.g. Fe, Cu). It has been found that the decomposition experienced in systems containing such transition metals can be inhibited by the presence of an effective amount of an organic epoxide.

It is contemplated that any epoxide compound having one or more of the required oxirane rings should provide some stabilizing effect and protection for the halopropynyl compound. That would include any compound having the following general structural formula:

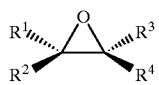

wherein $R^1$, $R^2$, $R^3$, and $R^4$ can be independently selected from a wide variety of radicals including hydrogen; an alkyl group of 1 to 20 carbon atoms such as methyl, ethyl, propyl, butyl, pentyl and the like; a substituted alkyl group; a halogen; a hydroxy; an aryl group; a substituted aryl group; an alkoxy group; an alkoxyalkyl group such as methoxymethyl, ethoxymethyl, propoxyethyl, n-butoxyethyl, tert-butoxymethyl, tert butoxybutyl and the like; a 2,3-epoxy di-alkoxy alkyl group, such as 2,3-epoxy-1-propoxyethoxymethyl, 2,3-epoxy-1-butoxyethoxyethyl and the like; an aryl group; an aralkyl group; an aryloxy group; an aryloxyalkyl group; or an alkanoyl group. $R^1$, $R^2$, $R^3$, or $R^4$ or may also be a radical of the formula:

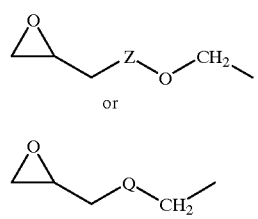

wherein Z is a straight or branched chain lower alkylene, for example propylene, butylene, pentylene, hexylene, heptylene and the like; or a halo substituted lower alkylene such as 2,2-dichloromethyl propylene. 2,2-dichloromethyl propylene and the like; and Q is ($C_1$–$C_4$) alkylene or carbonylarylcarboxy such as carbonylphenylcarboxy and the like; or one of $R^1$ or $R^2$ and one of $R^3$ or $R^4$ are joined together with the carbon to which they are attached, to form an alkylene chain of from 3 to 7 carbon atoms, which alkylene chain may be substituted with a lower alkylene to form a bicyclo alkane for example, bicyclo [3.1.1]heptane-bicyclo [2.2.2] octane and the like, or substituted with a lower alkenyl radical such as ethenyl, 1-methylethenyl, butenyl and the like; all of these groups may further be optionally substituted with one or more additional epoxide groups.

Among the epoxy compounds are those wherein $R^1$ is hydrogen, lower alkoxy, lower alkyl, or 2,3-epoxy-1-propoxyethoxymethyl, $R^2$ is hydrogen or lower alkyl, $R^3$ and $R^4$ are hydrogen, or $R^1$ or $R^2$ and one of $R^3$ or $R^4$ may be joined together with the carbon atom to which they are attached to form an alkylene chain of from 3 to 7 carbon atoms, which alkylene chain may be substituted with a lower alkylene to form a bicycloalkane.

The epoxides that are especially preferred are glycidyl ethers. These are compounds having one or more 2,3-epoxypropanoxy groups and can be represented by the general formula:

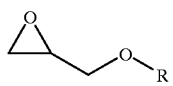

wherein R can defined the same as $R^1$, $R^2$, $R^3$ or $R^4$. A number of these glycidyl ethers are commercially available. The possibilities of glycidyl ethers are as numerous as the number of alcoholic groups from which they can be made by reacting the corresponding alcohol with a glycidyl halide such as glycidyl chloride (1-chloro-2,3-epoxy propane), or by reacting glycidyl alcohol with an appropriate halide.

Representative examples of suitable and preferred epoxides for use in the present invention include but are not restricted to:

carbon atoms. Examples of such radicals include methyl, ethyl, n-propyl, isopropyl, n-butyl, isobutyl, sec-butyl, tert-butyl, pentyl, iso-amyl, hexyl, octyl and the like. Alkyls often may be optionally substituted by an alkoxy (preferably a lower alkoxy), nitro, monoalkylamino (preferably a lower alkylamino), dialkylamino (preferably a di[lower] alkylamino), cyano, halo, haloalkyl (preferably trifluoromethyl), alkanoyl, aminocarbonyl, monoalkylamino-carbonyl, dialkylaminocarbonyl, alkyl amido (preferably lower alkyl amido), alkoxyalkyl (preferably a lower alkoxy [lower] alkyl), alkoxy-carbonyl, (preferably a lower alkoxy carbonyl) alkylcarbonyloxy (preferably a lower alkylcarbonyloxy) and aryl (preferably phenyl), said aryl being optionally substituted by halo, lower alkyl and lower alkoxy groups. The term "alkenyl", alone or in combination, means a straight-chain or branched-chain hydrocarbon radical having one or more double bonds and containing from 2 to about 18 carbon atoms preferably from 2 to about 8 carbon atoms. Examples of suitable alkenyl radicals include ethenyl, propenyl, allyl, 1,4-butadienyl and

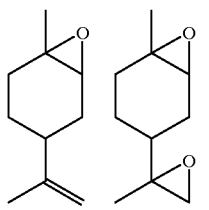

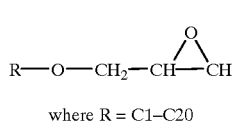

where R = C1–C20

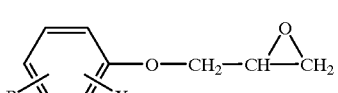

where R = H, alkyl, substituted alkyl
X = halogen

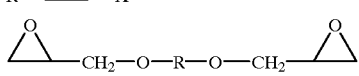

where R = C1–C20

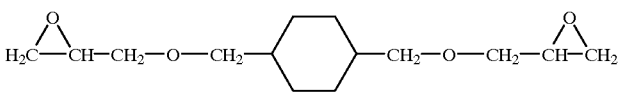

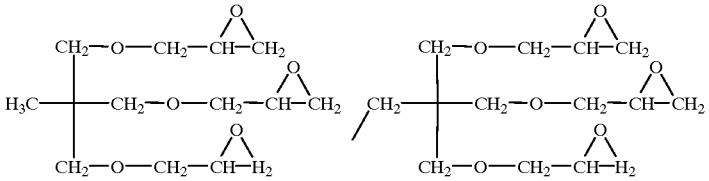

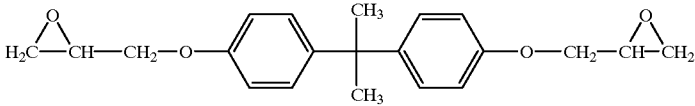

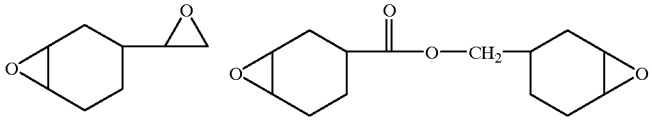

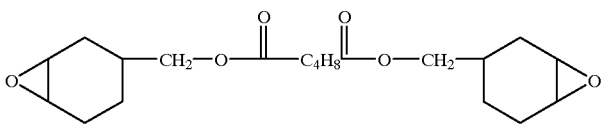

The term "alkyl", when used alone or in combination, means a straight-chain or branched-chain alkyl radical containing from 1 to about 20, preferably from 1 to about 12, the like. The term "alkoxy" as used alone or in combination herein refers to a straight or branched chain alkyl group covalently bonded to the parent molecule through an —O— linkage, i.e., an alkyl ether radical wherein the term alkyl is as defined above. Examples of suitable alkoxy radicals include methoxy, ethoxy, propoxy, isopropoxy, butoxy, n-butoxy, sec-butoxy, t-butoxy and the like. The term "alkenyloxy" refers to a straight-chain or branched-chain hydrocarbon radical having one or more double bonds covalently bonded to the parent molecule through an —O— linkage, i.e., an alkenyl ether radical wherein the term alkenyl is as defined above. The term "aryl", alone or in combination, means a carbocyclic aromatic system containing one, two or three rings wherein such rings may be attached together by one or more bonds. Examples of "aryl" include phenyl or naphthyl radicals either of which optionally carries one or more substituents selected from alkyl, alkoxy, halogen, hydroxy, amino and the like, such as p-tolyl, 4-methoxphenyl, 4-(tert-butoxy)phenyl, 4-fluorophenyl, 4-chlorophenyl, 4-hydroxyphenyl, 1-naphthyl, 2-naphthyl, and the like. Phenyl is generally preferred. The term "aralkyl", alone or in combination, means an alkyl radical as defined above in which one hydrogen atom is replaced by an aryl radical as defined above, such as benzyl, 2-phenylethyl and the like. Examples of substituted aralkyl include 3,5-dimethoxybenzyl, 3,4-dimethoxybenzyl, 2,4-dimethoxybenzyl, 3,4,5-trimethoxybenzyl, 2,6-dichlorobenzyl, and 1,4-bis(chloromethyl)benzene. The term "halogen" means fluorine, chlorine, bromine or iodine; chlorine generally is preferred. The term "alkanoyl", alone or in combination, means an acyl radical derived from an alkanecarboxylic acid wherein alkane means a radical as defined above for alkyl. Examples of alkanoyl radicals include acetyl, propionyl, butyryl, valeryl, 4-methylvaleryl, and the like. The term "alkoxy carbonyl", alone or in combination, means a radical of the formula —C(O)—O— alkyl in which the term "alkyl" has the significance given above. The term "aralkoxy carbonyl", alone or in combination, means a radical of the formula —C(O)—O— aralkyl in which the term "aralkyl" has the significance given above. An example of an aralkoxycarbonyl radical is benzyloxycarbonyl. The term "carboxy" means a radical of the formula R—C(O)—O— where R may be an alkyl or alkenyl group.

The amount of halopropynyl compound that may be required as a preservative in this invention may be dependent on the nature and type of the composition to be preserved. In accordance with the invention, the halopropynyl compound can be included in a final formulation for use in such applications as paints, coatings, etc. in a broad range from about 0.004% to 5.0% active concentration, more usually in a range from about 0.01% to 2%. Such compositions can be prepared from highly concentrated compositions of the active ingredients by appropriate dilution. The optimum useful range is normally about 0.1% to 0.5% of halopropynyl compound in the final formulations for such end use systems. With the use of such formulations in end use systems, it is possible to protect surfaces as well as other substrates for extended periods of time against microbial growth.

The amount of epoxide used may be dependent on the epoxide used, the nature of the composition, the nature and amount of the transition metal present, the amount of halopropynyl compound present and the relative concentrations of each. It is within the skill of the ordinary practitioner to make a proper adjustment when necessary.

The epoxide will normally be added in an amount of from about 10% to 400% by weight of the halopropynyl compound and more usually from 10% to 300% by weight. The preferred amount of epoxide required could depend on the type and amount of transition metal present. (The typical coating composition such as an alkyd paint would contain from about 0.005 to about 0.15 percent by weight of a transition metal (e.g. cobalt) drier.) It is preferred to add the epoxide in an amount that is about 50% to 300% by weight of the halopropynyl compound with 100% to 200% being especially preferred.

The stabilized antimicrobial compositions of the present invention will generally be formulated by mixing the epoxide components in a selected proportion relative to the halopropynyl compound in a liquid vehicle for dissolving or suspending the active components. The present invention specifically contemplates the preparation of concentrates comprising a halopropynyl compound and an organic epoxide in a liquid vehicle. These concentrates could be added into the particular nonaqueous formulation to be preserved such as, for example, an alkyd based coating formulation.

Suitable liquid vehicles for the stabilized antimicrobial compositions of this invention, particularly the preferred iodopropynyl butyl carbamate and a suitable organic epoxide are several glycol ethers and esters like propylene glycol n-butyl ether, propylene glycol tert-butyl ether, propylene glycol methyl ether, dipropyleneglycol methyl ether, tripropylenelene glycol methyl ether, propylene glycol n-butyl ether and the esters of the previously mentioned compounds. Other useful solvents are n-methyl pyrrolidone, n-pentyl propionate and dibasic esters of several dicarboxylic acids and mixes thereof.

In many applications, a preferred liquid vehicle for these products can be selected from n-methyl pyrrolidone, propylene glycol n-butyl ether, 1-methoxy-2-propanol, and the dibasic isobutyl ester blend of succinic, glutaric and adipic acids.

When preparing such antimicrobial formulations of the present invention for specific applications, the composition also will likely be provided with other adjuvants conventionally employed in compositions intended for such applications such as organic binding agents, additional antimicrobials, auxiliary solvents, processing additives, fixatives, plasticizers, dyes, color pigments, siccatives, corrosion inhibitors, antisettlement agents, anti-skinning agents and the like. Additional adjuvants used in the composition are preferably soluble in the liquid vehicle.

According to the present invention, substrates are protected from infestation by microorganisms simply by treating said substrate with a composition of the present invention. Such treating may involve mixing the composition with the substrate, coating or otherwise contacting the substrate with the composition and the like.

The following examples are presented to illustrate and explain the invention. Unless otherwise indicated, all references to parts and percentages are based on weight.

EXAMPLES

In the following examples, accelerated stability tests were carried out by putting the samples in narrow mouth jars (60 mL–100 mL.) and keeping them in a constant temperature oven at 45° C. (113° F.) for examples 1–4 and 50° C. (122° F.) for examples 5–11.

The decomposition of IPBC was followed by high pressure liquid chromatography using a reversed phase C-18 HPLC column [Waters, symmetry 150 mm length, 3.0 mm ID, flow rate 1 mL/min.] The mobile phase was a mixture of acetonitrile and water. The Waters instrument was equipped with a photodiode array (PDA) detector. IPBC was detected & calibrated at 230 nm.

Examples 1–3

Examples 1–3 are included to demonstrate the degradation of haloalkynyl compounds caused by transition metals. The stability of 3-iodo-2-propynyl butylcarbamate (IPBC) in Dowanol PnB, (Dow Chemical Corporation) was examined. (This solvent is widely used in the paints and coatings industry and provides sufficient solubility of the IPBC, the transition metal driers and the pigments commonly used.) Chosen for this investigation to illustrate the degradation caused by the transition metals were the manganese and cobalt octanoates widely used in the industry. The first example serves as a control and illustrates the stability of IPBC in the solvent, Dowanol PnB in the absence of a transition metal. Examples 2 and 3 illustrate the stability of IPBC in the presence of a transition metal. The data demonstrates the destructive effect that the presence of a transition metal has on the stability of IPBC.

Example 1

A 10% solution of IPBC was prepared by dissolving 5.0 g Troysan Polyphase® P100 in 45.0 g Dowanol PnB. The solution was heat aged at 45° C. for six weeks and was analyzed for the IPBC content at about one week intervals by HPLC. The results are presented in Table 1.

TABLE 1

Stability of IPBC in Dowanol PnB at 45° C.

| Time in Days | 0 | 9 | 15 | 23 | 28 | 34 | 42 |
|---|---|---|---|---|---|---|---|
| % IPBC | 10 | 9.9 | 9.8 | 9.8 | 9.9 | 9.9 | 9.7 |

This example shows that in the absence of a transition metal, the IPBC is relatively stable at 45° C. over the six week period.

Example 2

A solution of IPBC was prepared by dissolving 5.0 g Troysan Polyphase® P100 in 44.17g Dowanol PnB. To this solution was added 0.83 g Troymax® Manganese 6% and the resulting solution was aged at 45° C. for six weeks and was analyzed for the IPBC content at about one week intervals. The results are presented in Table 2.

TABLE 2

Stability of IPBC in the presence of Manganese drier at 45° C.

| Time in Days | 0 | 9 | 15 | 23 | 28 | 34 | 42 |
|---|---|---|---|---|---|---|---|
| % IPBC | 10 | 9.8 | 9.4 | 8.6 | 8.1 | 7.7 | 6.9 |

This example shows that in the presence of Manganese, about 30% of the IPBC was destroyed over the six week period.

Example 3

A solution of IPBC was prepared by dissolving 5.0 g Troysan Polyphase® P100 in 44.17 g Dowanol PnB. To this solution was added 0.83 g Troymax Cobalt® 6% and the resulting solution was aged at 45° C. for six weeks and was analyzed for the IPBC content at about one week intervals. The results are presented in Table 5.

TABLE 3

Stability of IPBC in the presence of Cobalt at 45° C.

| Time in Days | 0 | 9 | 15 | 23 | 28 | 34 | 42 |
|---|---|---|---|---|---|---|---|
| % IPBC | 10 | 6.4 | 4.5 | 2.6 | 1.7 | 1.6 | 0.4 |

This example shows that in the presence cobalt nearly all the IPBC was destroyed over the six week period.

Example 4

In this example, the stability of IPBC was evaluated in the presence of several alkyd resins, both in the presence of a cobalt drier (Recipe B) and in the absence of a cobalt drier (Recipe A).

A series of alkyd compositions without pigment were prepared by using the alkyd resins listed in Table 4 in the following general recipe A:

Recipe A

| Alkyd Resin | 60.0% |
|---|---|
| IPBC | 0.5% |
| Dowanol PnB | 1.3% |
| Methylethylketoxime | 0.2% |
| Mineral Spirits | 38.0% |

A series of alkyd compositions (without pigment) were prepared by using the alkyd resins listed in Table 4 in the following general recipe B:

Recipe B

| Alkyd Resin | 60.0% |
|---|---|
| IPBC | 0.5% |
| Dowanol PnB | 1.3% |
| Methylethylketoxime | 0.2% |
| Mineral Spirits | 37.5% |
| Cobalt Drier 6% | 0.5% |

The alkyds prepared as above were heat aged at 45° C. for four weeks and analyzed for residual IPBC by HPLC at one week intervals. The results are presented in Table 4.

TABLE 4

Stability of IPBC at 45° C. in various alkyd formulations

| | Residual % IPBC | | | | |
|---|---|---|---|---|---|
| Alkyd Resin | Initial | 1 Week | 2 Weeks | 3 Weeks | 4 Weeks |
| | Recipe A | | | | |
| Cargill 50-5070 | 0.55 | 0.52 | 0.5 | 0.47 | 0.47 |
| Duramac 2033 | 0.5 | 0.55 | 0.5 | 0.51 | 0.51 |
| Drisoy G-1 | 0.5 | 0.53 | 0.5 | 0.51 | 0.51 |
| Admerol 75-M-70 | 0.53 | 0.49 | 0.51 | 0.5 | 0.5 |
| Finnresin TA 8200 | 0.48 | 0.49 | 0.45 | 0.48 | 0.49 |
| | Recipe B | | | | |
| Cargill 50-5070 | 0.56 | 0.02 | ND[1] | ND | ND |
| Duramac 2033 | 0.5 | 0.02 | ND | ND | ND |
| Drisoy G-1 | 0.54 | 0.06 | ND | ND | ND |
| Amerol 75-M-70 | 0.5 | ND | ND | ND | ND |
| Finnrein TA 8200 | 0.67 | 0.04 | ND | ND | ND |

[1]ND means none detected

This example shows that in a typical alkyd base formulation, using a number of typical alkyd resins (with no pigment) at the levels typically used, the IPBC is stable in the absence of cobalt for the four week duration of the test, but is gone in two weeks in those examples where cobalt was present.

Examples 5–8

In each of these examples, the test compositions were prepared as follows. First a stock solution was prepared for each concentration of epoxide to be tested which contained the IPBC at a concentration of 20%, the epoxide at the concentration to be tested (5 to 45%) and a suitable solvent, N-methyl-2-pyrrolidinone, as the remainder (35% to 75%).

The stability tests were run using solvent based formulations (see below) without pigment (Formula I) and with pigment (Formula II).

Formula I—Solvent Based Coating Formulation Without Pigment

| Ingredient | % Present |
|---|---|
| Alkyd Resin | 20–25 |
| Bentone Solids | 1 |
| Methylethylketoxime | 0.9 |
| High Flash White Spirts | 63–70 |
| 3-Iodopropynyl Butyl Carbamate | 0.8 |
| Solvents Associated with Additives | 0.9–9 |
| Driers (Mixture of Co/Zr) | 0.3 |

Formula II—Solvent Based Coating Formulation With Pigment

| Ingredient | % |
|---|---|
| Pigment | 1 |
| 3-Iodopropynyl Butyl Carbamate | 0.5 |
| Solvents, binder, driers and other additives | 98.5 |

Example 5

In this example, three samples were prepared. In the first, the control, a sample of Formula I containing 0.8% IPBC, but no epoxide was prepared. In the second, a stock solution containing 5% Araldite DY 027 (Ciba Speciality Chemicals Corp.) as the epoxide was added to about 100 g grams of Formula I in an amount sufficient to bring the IPBC level to 0.8% and the epoxide level to 0.2%. In the third, a stock solution containing Araldite DY 027 at 35% was added to about 100 grams of Formula I in an amount sufficient to bring the IPBC level to 0.8% and the epoxide level to 1.4%. Each sample was placed in a tightly capped 200 mL narrow mouth jar and kept at 50° C. for four weeks. The IPBC content was measured at two and four weeks using High Pressure Liquid Chromatography as described above.

TABLE 5

| | % IPBC | | |
|---|---|---|---|
| % Araldite DY 027 | Initial | Two Weeks | Four Weeks |
| NONE | 0.8 | 0.45 | 0.05 |
| 0.2% | 0.8 | 0.76 | 0.70 |
| 1.4% | 0.8 | 0.76 | 0.78 |

This example 5 shows that even at a ratio of Epoxide: IPBC of as little as 1:4, the IPBC can be stabilized.

Example 6

In this example, a stock solution containing 40% Glydex N-10, (supplied by Exxon Chemical) as the epoxide, was added to each of five 100 gram samples of formula II in an amount sufficient to bring the IPBC concentration to 0.5%, and the epoxide to 1%. Each of said samples also contained a different pigment supplied by BASF or ICI. The pigments were blue pigments B 650 and B 622, green pigment G 735, red pigment R 568 and a transparent iron oxide pigment. Everything else was repeated as set forth in Example 5. (The green and blue pigments contain copper so that the formulations with these pigments would contain both cobalt and copper. The red pigment contained no transition metal itself, but the formulation containing the pigment was formula II which contained cobalt.) The results are presented in Table 6.

TABLE 6

Stability of IPBC in Presence of Various Pigments at 50° C. for Four Weeks.

| | | % IPBC | | |
|---|---|---|---|---|
| Additive | Pigment | Initial | Two Weeks | Four Weeks |
| Glydex N-10 | B650 | 0.53 | 0.41 | 0.46 |
| Glydex N-10 | B622 | 0.5 | 0.48 | 0.48 |
| Glydex N-10 | G735 | 0.51 | 0.48 | 0.48 |
| Glydex N-10 | R568 | 0.47 | 0.49 | 0.5 |
| Glydex N-10 | Iron Oxide | 0.49 | 0.47 | 0.49 |
| No Epoxide | B650 | 0.49 | ND[1] | ND |
| No Epoxide | B622 | 0.48 | ND | ND |
| No Epoxide | G735 | 0.48 | ND | ND |
| No Epoxide | R568 | 0.5 | 0.27 | 0.11 |
| No Epoxide | Iron Oxide | 0.48 | 0.23 | 0.12 |

[1]ND means none detected

This example shows once again that the epoxide protects the IPBC against degradation in the presence of cobalt, copper and iron.

Example 7

In this example a stock solution containing 45% of the epoxide Araldite DY025 (Ciba Specialty Corp.) was used with 5 samples of Formula II containing the same pigments as used in Example 6. Everything else was repeated as set forth in Example 6. The IPBC level was at 0.5% and the epoxide was at 1.1%. The results are set forth in Table 7.

TABLE 7

Stability of IPBC in Presence of Various Pigments at 50° C. for Four Weeks

| | | % IPBC | | |
|---|---|---|---|---|
| Additive | Pigment | Initial | Two Weeks | Four Weeks |
| Araldite DY025 | B650 | 0.51 | 0.39 | 0.41 |
| Araldite DY025 | B622 | 0.46 | 0.44 | 0.28 |
| Araldite DY025 | G735 | 0.53 | 0.52 | 0.5 |
| Araldite DY025 | R568 | 0.52 | 0.51 | 0.51 |
| Araldite DY025 | Iron Oxide | 0.52 | 0.49 | 0.47 |
| No Epoxide | B650 | 0.49 | ND | ND |
| No Epoxide | B622 | 0.48 | ND | ND |
| No Epoxide | G735 | 0.48 | 0.08 | ND |

TABLE 7-continued

Stability of IPBC in Presence of Various Pigments at 50° C. for Four Weeks

| | | % IPBC | | |
|---|---|---|---|---|
| Additive | Pigment | Initial | Two Weeks | Four Weeks |
| No Epoxide | R568 | 0.5 | 0.27 | 0.11 |
| No Epoxide | Iron Oxide | 0.48 | 0.23 | 0.12 |

This example confirms the results of example 6 with another epoxide.

Example 8

In this example, 9 samples of Formula II containing the epoxides Heloxy R Modifier 67 at 10%, Heloxy R Modifier 62 at 30%, Heloxy R Modifier 48 at 7.5%, Araldite DY 025 at 30%, Araldite GY 506 at 30%, Flexol LOE at 25%, Fexol EPO at 35% and Vikoflex 9010 at 30% and a sample with no epoxide. Everything else was repeated as set forth in Example 5, the IPBC level being at 0.5%. The results are presented in Table 8.

TABLE 8

Stability of IPBC in Presence of Green Pigment G735 at 50° C. for Four Weeks, Utilizing Various Epoxides.

| | % Epoxide in Formulation | % IPBC | | |
|---|---|---|---|---|
| Epoxide | A | Initial | Two Weeks | Four Weeks |
| Heloxy R Modifier 67 | 0.25 | 0.48 | 0.47 | 0.02 |
| Heloxy R Modifier 62 | 0.75 | 0.48 | 0.48 | 0.44 |
| Heloxy R Modifier 48 | 0.2 | 0.49 | 0.21 | ND |
| Araldite DY025 | 0.75 | 0.49 | 0.39 | 0.16 |
| Araldite GY506 | 0.75 | 0.54 | 0.53 | 0.50 |
| Flexol LOE | 0.6 | 0.51 | 0.06 | ND |
| Flexol EPO | 0.9 | 0.51 | 0.03 | ND |
| Vikoflex 9010 | 0.75 | 0.59 | 0.13 | ND |
| None | — | 0.48 | 0.08 | ND |

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A nonaqueous composition containing a transition metal and an antimicrobial halopropynyl compound wherein the stability of said antimicrobial halopropynyl compound in said nonaqueous composition is improved by the presence of an effective amount of an organic epoxide.

2. The composition of claim 1 wherein the halopropynyl compound is an iodopropynyl derivative selected from the group consisting of an iodopropynyl ester, an iodopropynyl ether, an iodopropynyl acetal, an iodopropynyl carbamate and an iodopropynyl carbonate.

3. The composition of claim 2 wherein the halopropynyl compound is an iodopropynyl carbamate of the formula:

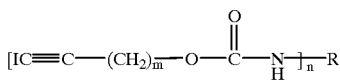

wherein R may have one to three linkages corresponding to n and is selected from the group consisting of hydrogen, substituted and unsubstituted alkyl, aryl, alkylaryl, and aralkyl groups having from 1 to 20 carbon atoms and cycloalkyl and cycloalkenyl groups of 3 to 10 carbon atoms, and m and n are independent integers from 1 to 3.

4. The composition of claim 3 wherein the iodopropynyl carbamate is 3-iodo-2-propynyl butyl carbamate.

5. The composition of claim 4 wherein the organic epoxide is a glycidyl ether.

6. The composition of claim 5 wherein there is present a transition metal selected from the group consisting of cobalt, manganese, copper, iron, cerium, vanadium, chromium, nickel and zinc.

7. The composition of claim 6 wherein the nonaqueous composition is an alkyd coating composition.

8. The composition of claim 7 wherein the alkyd coating composition is an alkyd paint.

9. The composition of claim 7 wherein the 3-iodo-2-propynyl butyl carbamate and the organic epoxide are present in a proportion of from about 1 part 3-iodo-2-propynyl butyl carbamate to 5 parts organic epoxide to about 5 parts 3-iodo-2-propynyl butyl carbamate to 1 part organic epoxide.

10. The composition of claim 8 wherein the 3-iodo-2-propynyl butyl carbamate and the organic epoxide are present in a proportion of from about 1 part 3-iodo-2-propynyl butyl carbamate to 5 parts organic epoxide to about 5 parts 3-iodo-2-propynyl butyl carbamate to 1 part organic epoxide.

11. The composition of claim 9 containing from about 0.004% to 5.0% of said halopropynyl compound.

12. The composition of claim 10 containing from about 0.004% to 5.0% of said halopropynyl compound.

13. The composition of claim 11 wherein cobalt, manganese, iron or copper is present.

14. The composition of claim 13 wherein cobalt is present.

15. The composition of claim 13 wherein the glycidyl ether is an aryl glycidyl ether.

16. The composition of claim 12 wherein cobalt, manganese, iron or copper is present.

17. The composition of claim 16 wherein cobalt is present.

18. The composition of claim 16 wherein the glycidyl ether is an aryl glycidyl ether.

19. A stabilized antimicrobial composition suitable for inhibiting antimicrobial growth in a nonaqueous composition containing a transition metal which comprises an iodopropynyl carbamate of the formula:

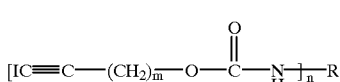

wherein R may have one to three linkages corresponding to n and is selected from the group consisting of hydrogen, substituted and unsubstituted alkyl, aryl, alkylaryl, and aralkyl groups having from 1 to 20 carbon atoms and cycloalkyl and cycloalkenyl groups of 3 to 10 carbon atoms, and m and n are independent integers from 1 to 3 and an effective amount of an organic epoxide.

20. The composition of claim 19 wherein the iodopropynyl carbamate is 3-iodo-2-propynyl butyl carbamate.

21. The composition of claim 20 wherein the organic epoxide is a glycidyl ether.

22. The composition of claim 21 wherein the 3-iodo-2-propynyl butyl carbamate and the organic epoxide are present in a proportion of from about 1 part 3-iodo-2-propynyl butyl carbamate to 5 parts organic epoxide to about 5 parts 3-iodo-2-propynyl butyl carbamate to 1 part organic epoxide.

23. The composition of claim 22 wherein the glycidyl ether is an aryl glycidyl ether.

24. A method for inhibiting microbial infestation in the presence of a transition metal selected from the group consisting of cobalt, manganese, copper, iron, cerium, vanadium, chromuim, nickel and zinc in a nonaqueous composition normally subject to microbial infestation which comprises adding thereto an effective inhibiting amount of a composition which comprises the 3-iodo-2-propynyl butyl carbamate and an effective amount of an organic epoxide.

25. The method of claim 24 wherein the organic epoxide is a glycidyl ether.

26. The method of claim 25 wherein the nonaqueous composition is an alkyd coating composition.

27. The method of claim 26 wherein the alkyd coating composition is an alkyd paint.

28. The method of claim 26 wherein the 3-iodo-2-propynyl butyl carbamate and the organic epoxide are present in a proportion of from about 1 part 3-iodo-2-propynyl butyl carbamate to 5 parts organic epoxide to about 5 parts 3-iodo-2-propynyl butyl carbamate to 1 part organic epoxide and the level of halopropynyl compound in the final product is from about 0.004% to 5.0% of said final product.

29. The method of claim 27 wherein the 3-iodo-2-propynyl butyl carbamate and the organic epoxide are present in a proportion of from about 1 part 3-iodo-2-propynyl butyl carbamate to 5 parts organic epoxide to about 5 parts 3-iodo-2-propynyl butyl carbamate to 1 part organic epoxide and the level of halopropynyl compound in the final product is from about 0.004% to 5.0 of said final product.

30. The method of claim 28 wherein cobalt, manganese, iron or copper is present.

31. The method of claim 30 wherein cobalt is present.

32. The method of claim 30 wherein the glycidyl ether is an aryl glycidyl ether.

33. The method of claim 29 wherein cobalt, manganese, iron or copper is present.

34. The method of claim 33 wherein cobalt is present.

35. The method of claim 33 wherein the glycidyl ether is an aryl glycidyl ether.

* * * * *